US009757037B2

United States Patent
Schibler et al.

(10) Patent No.: US 9,757,037 B2
(45) Date of Patent: Sep. 12, 2017

(54) IN VIVO BIOLUMINESCENCE MONITORING APPARATUS

(75) Inventors: Ueli Schibler, Borex (CH); Andre Liani, Hermance (CH); Camille Saini, Geneva (CH); Luigi Bonacina, Lausanne (CH); Jean-Pierre Wolf, Geneva (CH)

(73) Assignee: UNIVERSITE DE GENEVE, Geneva (CH)

( * ) Notice: Subject to any disclaimer, the term of this patent is extended or adjusted under 35 U.S.C. 154(b) by 680 days.

(21) Appl. No.: 14/112,641

(22) PCT Filed: Apr. 17, 2012

(86) PCT No.: PCT/IB2012/051916
§ 371 (c)(1),
(2), (4) Date: Oct. 18, 2013

(87) PCT Pub. No.: WO2012/143854
PCT Pub. Date: Oct. 26, 2012

(65) Prior Publication Data
US 2014/0046195 A1    Feb. 13, 2014

Related U.S. Application Data

(60) Provisional application No. 61/476,346, filed on Apr. 18, 2011.

(51) Int. Cl.
*A61B 5/00* (2006.01)
*A01K 1/03* (2006.01)
(Continued)

(52) U.S. Cl.
CPC ............ *A61B 5/0059* (2013.01); *A01K 1/031* (2013.01); *A01K 29/005* (2013.01); *G01N 21/763* (2013.01)

(58) Field of Classification Search
CPC .. A61B 5/0059; A61B 1/00089; A01K 1/031; A01K 29/005; G01N 21/763
See application file for complete search history.

(56) References Cited

U.S. PATENT DOCUMENTS 3,367,308 A  *  2/1968  Quattrone .............. A01K 1/031
                                                    119/420
4,787,382 A  * 11/1988  Pekovic ................... A61D 7/04
                                                    119/421
(Continued)

FOREIGN PATENT DOCUMENTS

| WO | WO 98/30254    | 7/1998  |
| WO | WO 01/63247    | 8/2001  |
| WO | WO 2009/144309 | 12/2009 |

OTHER PUBLICATIONS

Written Opinion in International Application No. PCT/IB2012/051916, Aug. 2, 2013, pp. 1-7.

*Primary Examiner* — Long V Le
*Assistant Examiner* — Colin T Sakamoto
(74) *Attorney, Agent, or Firm* — Saliwanchik, Lloyd & Eisenschenk

(57) ABSTRACT

Apparatus for real-time in vivo bioluminescence monitoring in a conscious small animal, comprising a light-tight enclosure (4) with a base (16), side wall (19) and cover (20) configured for housing the small animal such that it may move freely, a bioluminescence detector system (6) comprising a light detector (22) for detecting the light emitted by said small animal connected to a data processing system, and a life-sustaining system (8) configured for maintaining the small animal alive for a prolonged period of time spanning from a few days to a few weeks.

20 Claims, 2 Drawing Sheets

(51) Int. Cl.
*A01K 29/00* (2006.01)
*G01N 21/76* (2006.01)

(56) References Cited

U.S. PATENT DOCUMENTS

| | | | | |
|---|---|---|---|---|
| RE32,970 E | * | 7/1989 | Furlani | A01K 39/0113 |
| | | | | 119/52.3 |
| 5,299,529 A | * | 4/1994 | Ramirez | A01K 5/0291 |
| | | | | 119/51.11 |
| 5,352,886 A | * | 10/1994 | Kane | G01J 1/04 |
| | | | | 250/208.2 |
| 6,775,567 B2 | * | 8/2004 | Cable | G01N 21/01 |
| | | | | 600/407 |
| 7,659,387 B1 | * | 2/2010 | Tei | A01K 67/0275 |
| | | | | 435/325 |
| 2004/0081621 A1 | | 4/2004 | Arndt et al. | |
| 2004/0144328 A1 | * | 7/2004 | Bonner | A01K 1/03 |
| | | | | 119/455 |
| 2005/0175538 A1 | | 8/2005 | Coquoz et al. | |

* cited by examiner

IN VIVO BIOLUMINESCENCE MONITORING APPARATUS

CROSS-REFERENCE TO RELATED APPLICATIONS

This application is the U.S. national stage application of International Patent Application No. PCT/IB2012/051916, filed Apr. 17, 2012, which claims the benefit of U.S. Provisional Patent Application No. 61/476,346, filed Apr. 18, 2011.

FIELD OF INVENTION

This invention relates to an apparatus and a method for non-invasive real-time in vivo bioluminescence monitoring in a small animal.

BACKGROUND

In many biomedical fields it is required to record acute signaling events which reflect biological pathways or mechanisms. One common method of monitoring gene expression in a living cell, tissue or animal relies on the use of a luminescent reporter gene placed under the control of a gene of interest in said cell, tissue or animal. The activity of genes can be visualized in real-time either by fluorescence or bioluminescence recording of transgenic cells or organisms expressing fluorescent proteins or luciferase, respectively.

Both of these techniques have been successfully adapted to whole-body imaging of mice (Hoffman and Yang (2006) *Nat. Protoc* 1, 1429-1438; Sandhu et al. (2010) *Wiley Interdiscip Rev Syst Biol Med* 2, 398-421). However, in most applications the animals were anesthetized to allow for long exposure times and expressed reporter genes that were driven by strong, constitutively active promoters and that specified mRNAs and/or proteins with long half-lives. As the steady-state accumulation of an mRNA or a protein equals synthesis rate (S) times half-life ($T_{1/2}$) divided by the natural logarithm of 2 ($ST_{1/2}/\ln2$), and since the number of photons is directly proportional to the cellular concentration of the fluorescent or luminescent proteins, such reporter genes produce strong and thus readily detectable signals.

For particular studies, such as the recording of circadian gene expression, the genes are less potently transcribed and the reporter gene products (mRNA and protein) are short-lived. As a result, the luminescent or fluorescent proteins accumulate to relatively low concentrations and hence produce only relatively weak signals. Yet frequent image acquisition over extended time periods (several days) are required in such studies, and this obviously precludes anesthesia (and thus long exposure times) of the animals under investigation. Moreover, conventional fluorescence measurements imply excitation with bright light, which would be likely to phase-shift animals during the recording. Therefore, bioluminescence monitoring would be a more judicious method for tracking rhythmic gene expression.

The IVIS Kinetic® system from Caliper Life Sciences provides a real-time, fast imaging system enabling acquisition of biologically relevant events within milliseconds. However, the signal can only be detected for a few minutes at most. When combined with an isolation chamber, this system allows bioluminescence to be monitored in conscious animals.

Despite its usefulness, the technology of the prior art cannot be applied to experimental conditions where bioluminescence is expressed in tissues containing a small number of cells, such as skin, skeletal and heart muscle, kidney, parts of the intestine, spleen, and exocrine pancreas, nor does it allow, for instance, the long-term monitoring of circadian gene expression in tissues of freely moving individual animals.

With the technology of the prior art, signal strength may be a limiting factor as well as the duration of the monitoring of the bioluminescence signal. Moreover, the technology of the prior art does not allow the effect of controlled environmental conditions including food, light, medicaments, etc. to be studied.

Therefore, there is still a need to further provide a technology and apparatus for real-time in vivo bioluminescence monitoring in a small animal allowing a high temporal resolution, with a minimal background noise, on a long term such as several days or several weeks, and in controlled environmental conditions.

The apparatus and method of the invention solve this problem and could find applications in circadian, ultradian, or infradian biology, for instance, but should also, without being limited to these examples, readily reveal the kinetics of signaling by hormones, cytokines, neuronal pathways, and metabolites such as bile acids, cholesterol, fatty acids, glucose, oxygen, and medical drugs, or allow measurement of the expression of the genes of the cellular cycle in sane and cancerous tissues, or the expression of the genes related to physical activity.

SUMMARY OF THE INVENTION

An object of this invention is to provide an apparatus for real-time in vivo bioluminescence and/or fluorescence monitoring in a small animal allowing a high temporal resolution, with a minimal background noise.

It is advantageous to provide an apparatus for bioluminescence monitoring in a small animal over a long term between several days and several weeks.

It is advantageous to provide an apparatus for bioluminescence monitoring in a small animal that provides accurate and stable readings independently of the displacement and position of the small animal.

It is advantageous to provide an apparatus for bioluminescence monitoring in a small animal in controlled and easily reproducible environmental conditions.

It is advantageous to provide an apparatus for bioluminescence monitoring that is cost-effective to implement and efficient to operate.

Objects of this invention have been achieved by providing an apparatus for bioluminescence monitoring according to claim 1.

Disclosed herein is an apparatus for real-time in vivo bioluminescence monitoring in a conscious small animal, comprising a light-tight enclosure configured for housing the small animal such that it may move freely, a bioluminescence detector system for detecting the light emitted by said small animal connected to a data processing system (e.g., a personal computer), and a life-sustaining system configured for maintaining the small animal alive for a prolonged period of time spanning from a few days to a few weeks.

The life-sustaining system may comprise a food delivery device, a ventilation system, and a source of light all connected to the data processing system and remotely controllable by the data processing system.

The apparatus may further comprise a temperature sensor configured to measure the environmental temperature in the light-tight enclosure and a heat exchanger to control the environmental temperature, both connected to the data processing system and remotely monitored and controllable by the data processing system.

In an embodiment, the food delivery device comprises a feeding tube in which food may be inserted, the feeding tube comprising a window at a bottom end of the tube proximate a base of the light-tight enclosure configured for providing access to the food, the food delivery device further comprising a food access closure device connected to the data processing system and remotely actuatable to close access to food through the window. The food access closure device may comprise a closure tube coaxially and slidably mounted around the feeding tube and coupled to an actuator configured to lift or to rotate the closure tube to close or open the feeding window, respectively. The food may be in the form of pellets stacked vertically, the lowest pellet resting on a bottom end of the tube positioned at or just above the base.

The apparatus may advantageously comprise a light-funneling device inside the enclosure, comprising a light-funneling member that extends from the light detector (e.g., a photomultiplier tube (PMT)) mounted on a cover wall of the enclosure in a diverging manner towards a base of the enclosure. The light-funneling member comprises a substantially conical surface directed towards the base that is light-reflecting or light-diffusing or a combination of part reflecting and part diffusing and configured to minimize internal loss of light and to improve channeling of light emitted from the small animal to a light-collecting face of the light detector. The light-funneling device may further comprise a central light-redirecting portion protruding upwards from the base into the enclosure, comprising a surface that is light-reflecting or light-diffusing or a combination of part reflecting and part diffusing and configured to re-direct light emitted from the small animal towards the surface of light funneling member.

Advantageously, the light-tight enclosure has a cylindrical or generally cylindrical shape, or at least the base of the enclosure has a circular or generally circular shape.

The apparatus may further comprise an animal activity-related system comprising a movement detector such as a passive infrared sensor and/or an activity station such as a voluntary running wheel.

The delivery of food, liquid, light, and the temperature in the light-tight enclosure may advantageously be controlled by the data processing system.

Also disclosed herein is a method for non-invasive real-time in vivo bioluminescence monitoring in a small conscious animal comprising:

placing a small animal expressing a luminescent reporter gene under the control of a gene of interest in the apparatus; and monitoring the light emitted by said small animal which is detected by the bioluminescence detector system.

The small animal may be a rodent such as a mouse, a rat, or a hamster.

The luminescent reporter gene may be the gene encoding luciferase.

The small animal may be a transgenic animal or an animal in which at least one organ or tissue has been transduced with a vector harboring a luminescent reporter gene under the control of a gene of interest.

The small animal may have been injected with a substrate of the luminescent reporter gene's product, such as luciferin if luciferase is the reporter gene's product, prior to placing said animal in the light-tight enclosure.

Further objects and advantageous aspects of the invention will be apparent from the claims, and from the following detailed description and accompanying figures.

DETAILED DESCRIPTION OF AN EMBODIMENT OF THE INVENTION

Figure 1:
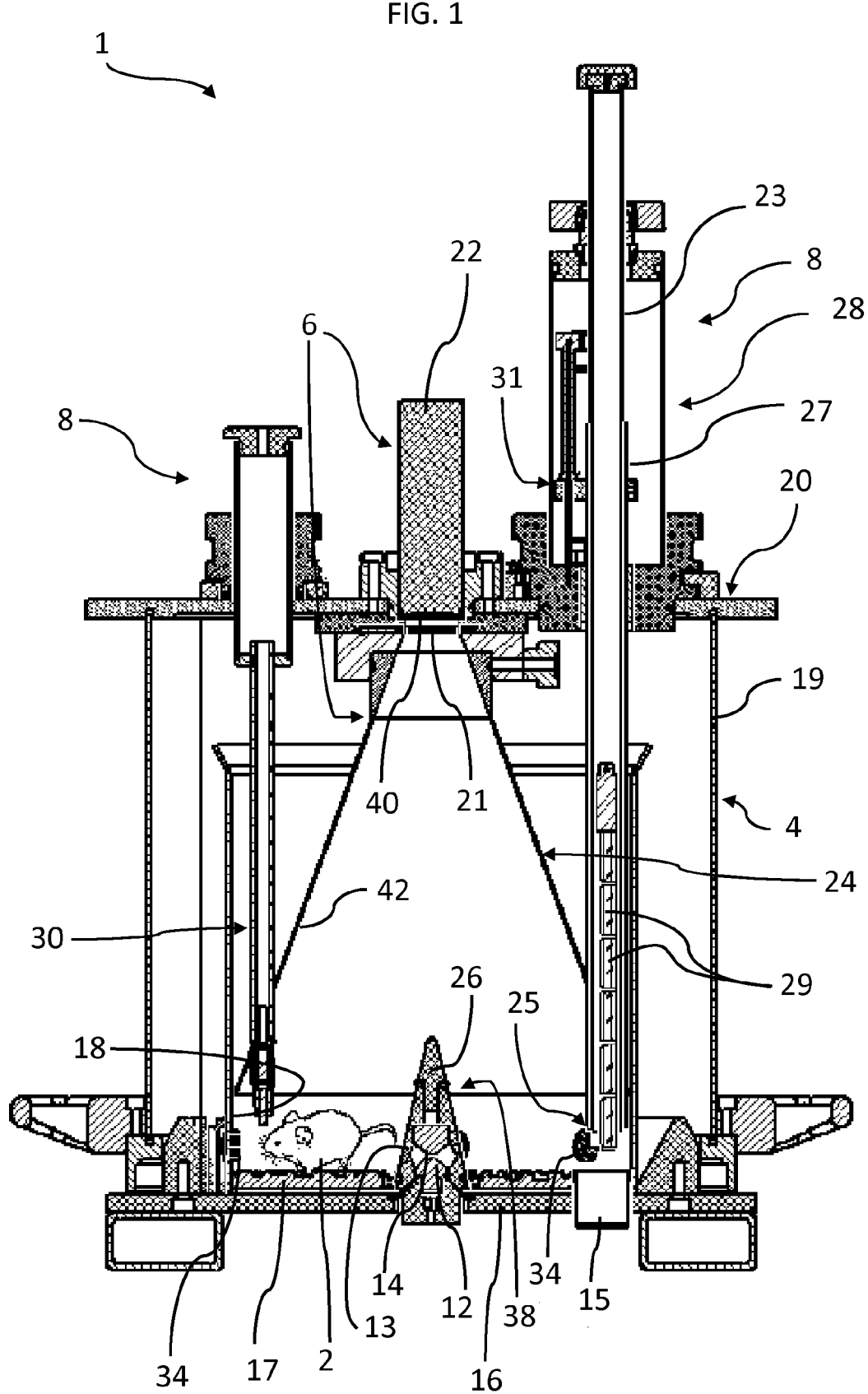
FIG. 1 is a schematic illustration in cross-section of an embodiment of a bioluminescence monitoring apparatus according to this invention.
Figure 2:
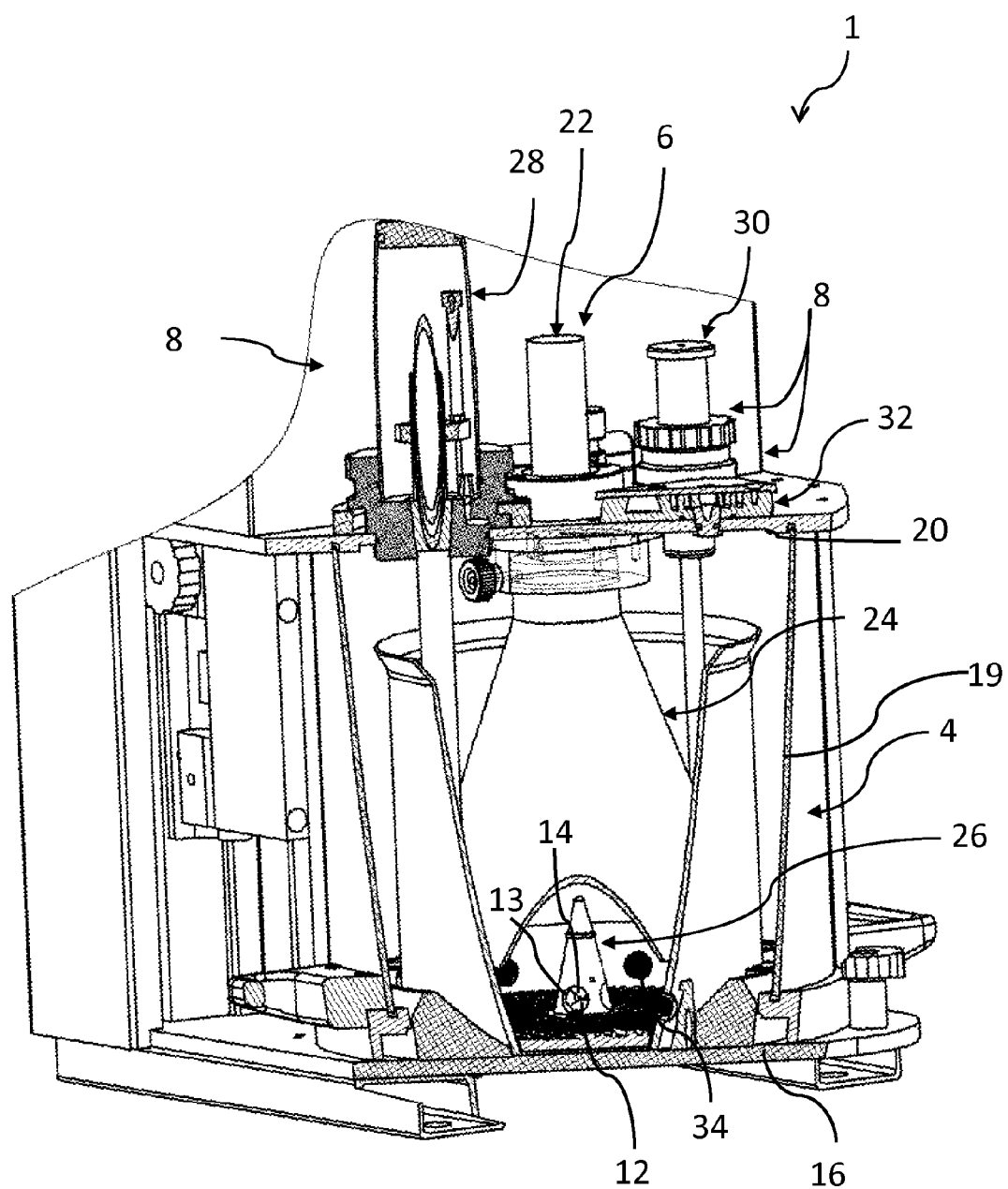
FIG. 2 is a schematic illustration in perspective and partial cross-section of the embodiment of FIG. 1.

Referring to the figures, an apparatus 1 for real-time in vivo bioluminescence monitoring in a small animal 2 comprises a light-tight enclosure 4, a bioluminescence detector system 6, and a life-sustaining and controlling system 8 to enable monitoring of bioluminescence from the small animal (e.g., a rodent) over an extended period of time, for example from a few days to a few weeks. The apparatus 1 may also be used for real-time in vivo fluorescence monitoring and measurement. For the sake of simplicity, reference to the term "bioluminescence monitoring" in the present description shall generally be understood to include "bioluminescence and/or fluorescence monitoring" unless the context dictates otherwise.

The small animal expresses a luminescent reporter gene under the control of a gene of interest. The luminescent reporter gene may in particular include a gene encoding luciferase, for instance firefly luciferase. The small animal may in particular be a transgenic animal or an animal in which at least one organ or tissue has been transduced with a vector harboring a luminescent reporter gene under the control of a gene of interest. The small animal may be a rodent (e.g., mouse, rat, hamster), or any other vertebrate (amphibian, reptile, bird) whose organs emit photons. The real-time in vivo monitoring in the present invention may advantageously be performed over a prolonged period of time spanning from a few days to a few weeks on a non-anesthetized conscious animal administered with a substrate of the luminescent reporter gene's product to produce light (e.g., luciferin). Administration of the substrate may for instance be by means of intraperitoneal or subcutaneous implantation of microosmotic Alzet pumps delivering luciferin for 1 to 2 weeks.

The apparatus may further include an animal activity-related system either for monitoring certain activities of the animal, such as its movements, or for generating animal activity depending on the experiment to be conducted. The apparatus may also include a drug administration system (not shown) for administering luciferin, anesthetics, or other drugs used in the in vivo monitoring process.

The apparatus 1, and in particular the bioluminescence detector system 6, is coupled to a data processing system (not shown), for instance a personal computer with software that may include an image acquisition and processing means for processing the data from the bioluminescence detector system and from the animal activity-related system. The data processing system may also include control software for operation of the life-sustaining system and animal activity-related and drug administration systems.

The light-tight enclosure 4 comprises a base 16, a side wall 19, and a cover 20. The base 16 may comprise, or be in the form of, a pull-out tray in order to clean the floor of the base member and insert or replace absorbent substrate 17 on the floor of the base, the substrate being for example straw, wood chippings, or other materials for the comfort of the small animal and for absorbing excrement and urine. The base 16 may advantageously have a circular or generally circular form and the side wall 18 a cylindrical or generally cylindrical form, this form reducing the influence of the position of the small animal on the base on the measurement results, such shape being well adapted for optimal detection of bioluminescence emitted by the small animal. The side wall may also comprise a door (not shown) or other displaceable entry or exit means to allow the small animal 2 to be placed in and removed from the light-tight enclosure. Instead of a door in the side wall, it may also be possible to have a removable cover 20, or to have the side wall and cover detachable from the base for lifting off the base.

The life-sustaining and controlling system 8 advantageously comprises a controllable and actionable food delivery device 28, a controllable and actionable liquid delivery device 30, a controllable ventilation system 32, and a controllable source of light 34. The various life-sustaining and controlling devices may advantageously be connected to the data processing system and remotely controlled. Nevertheless, some of these devices may in addition or alternatively be manually controllable. The life sustaining and controlling system enables the small animal to be kept in the light-tight enclosure for a prolonged period of time, while also controlling various stimuli, for instance those relevant to the circadian cycle and bioluminescence activity, such as the amount of food and/or water the animal receives, the time at which it receives food and/or water, or the time and duration of darkness and light.

In the illustrated embodiment, the food delivery device 28 comprises a feeding tube 23 in which food may be inserted, for example in the form of conventional pellets 29 typically used to feed small rodents. The pellets 29 drop down the tube 23 and are stacked vertically, the lowest pellet resting on a bottom end of the tube positioned at or just above the base 16. A window 25 at the bottom end of the tube 23 provides access to the food pellet by the small animal 2. The food delivery device 28 further comprises a food access closure device, which may comprise a closure tube 27 coaxially and slidably mounted around the feeding tube (as illustrated), or simply a movable plate (not shown) operable to cover the window 25 to block access to the food pellet. When access to food is given, the closure tube is lifted by means of an electrical, hydraulic or pneumatic actuator 31, which may optionally be remotely controlled and which drives the closure tube 27 upwards or in rotation, or by manual operation of the closure tube in situ. To prevent access to food, in a first variant the closure tube 27 is dropped or driven down so that it covers the window 25. In a second variant the closure tube 27 is movable in rotation and comprises a lateral orifice at its lower end corresponding to the feeding tube window 25, which may be aligned with the window 25 when access to food is given. In the second variant, access to food is blocked by rotating the closure tube until the closure tube orifice and the feeding tube window do not overlap. In a variant (not shown), the food access closure device may extend from the floor of the enclosure rather than from the top of the enclosure as shown.

The food delivery device may further include a lower trap or removable tray 15 positioned below the feeding tube 23 configured to capture the pieces of uneaten food that fall on the floor. The trap may be opened or the tray removed to access and weigh the uneaten food in order to measure the exact quantity of food eaten by the small animal.

Controlling feeding of the small animal enables the control of physiological functions and states of the animal that affect the animal's behavior and gene expression.

It may be noted that within the scope of this invention, it would be possible to have a single food and liquid delivery device, for example in circumstances where the food is in a liquid or semi-liquid form.

The ventilation system 32 may either be a passive ventilation system, such as a labyrinth through the light-tight enclosure that allows an exchange of air with the external environment, but prevents the passage of light, or could be an active ventilation system. An active ventilation system 32 may comprise an electrically actuated ventilator for the injection and circulation of ambient external air into the light-tight enclosure 4, and optionally in addition, or alternatively, a gas injection system for the injection of air or other gases, or a combination of both. In the latter variant, the ventilation system may also be used to inject gases at controlled times that are relevant for the experiment, for example gases with drugs and/or other components that affect the physiological activity and state of the small rodent, such as soporifics, stimulants, anesthetics, oxygen, humidity and fragrances. The ventilation system may further comprise a heat exchanger (not shown) that may be controlled to cool or heat the air introduced and circulating in the enclosure 4 in order to change and control the temperature of the air in the enclosure. For immune-suppressed animals (e.g., animals with genetic or experimentally induced deficiencies in the innate and adaptable immune system), the air may be filtered so as to remove airborne pathogens.

Varying and controlling the temperature level, for example generating cycles of relatively cold or warm temperatures for controlled duration in the animal's environment, may be used in certain experiments to affect the animal's behavior, physiological state, and gene expression.

One or more temperature sensors (not shown) placed in the enclosure 4 or on the walls of the enclosure may be provided. The temperature sensor(s) may be connected to the data processing system for monitoring the temperature in the small animal's environment. The temperature sensor(s) may also be used to control the ventilation system and heat exchanger to generate the desired temperature in the enclosure.

The light source 34 enables light stimuli to be generated for certain periods of time, in particular to affect the circadian behavior of the small animal. The light source may comprise one or more lights 34 positioned inside the enclosure. The light source may advantageously include a plurality of (for instance four circumferentially distributed) LEDs producing white light and/or light around a particular wavelength. The light sources may for instance be mounted on an inner side wall 18. During the light cycle, the bioluminescence detector may be switched off, and/or the detector system may comprise a shutter 21 configured to completely block light to the detector's light sensor. The shutter 21 may be driven by an electromechanical actuator that may be controlled remotely by the data processing system.

The animal activity-related system may comprise position or movement sensors 12 mounted in a central portion 38 of the enclosure 4 extending from the base member 16, and/or mounted on the inner side wall 18. The position or movement sensor, which may for instance include an infrared sensor or an ultrasound sensor, may be used to determine whether the animal is moving and/or used to determine the position of the animal or its distance from the center or side wall. A single sensor may be provided at a central position on the base, or on a side wall member 18 of the enclosure 4. In the embodiment illustrated, the position sensor comprises an infrared detector 12 placed inside the central portion 38 and in communication with the environment surrounding the small animal via orifices 13 in the central portion. In order to enhance capture of infrared emissions from the small animal to the infrared detector, the position sensor may further comprise a reflector 14, for instance in the form of an angled or conical mirror positioned inside the central portion above the detector 12 and configured to reflect infrared emissions from the small animal towards the infrared detector 12. It is also possible to provide a plurality of sensors on the side wall and other positions within the enclosure for detecting movement or position. The movement detector may be useful for monitoring activity of the small animal, for instance to determine whether the animal is resting or awake or eating.

The animal activity-related system may also comprise activity stations such as a voluntary running wheel or a treadmill device (not shown) to allow or to impose exercise on the small animal.

The animal activity-related system may further comprise sensors to measure the temperature, blood pressure, cardiac frequency and other physiological parameters of the small animal simultaneously to the measurement of gene activity. Certain measures, in particular body temperature and cardiac frequency, may be made without contacting the animal by infrared sensors or cameras positioned in the center or at the periphery of the light-tight enclosure. Other sensors may be implanted in or mounted on the small animal and transmit measurement signals wirelessly. Wireless sensors may for instance be configured as passive RF devices communicating with an RF base station mounted in the apparatus.

The apparatus may further optionally include a drug administration system, such as an injection system that may deliver luciferin, an anesthetic, or other drugs to the small animal, as needed for the experiment. It may be noted that the small animal may also be implanted with an implant for delivering luciferin in a continuous manner over the experimental period, for example one to two weeks. The drug administration system may also include administration of a drug in gaseous form via the ventilation system.

The bioluminescence detector system 6 may comprise a light detector 22 that could be a photon detector, a camera or any other form of photon-counting device. The photon detector may advantageously comprise a Photo-Multiplier Tube (PMT). The detector may also comprise an Electron Multiplying Charge Coupled Device (EM-CCD). For simplicity, we shall hereinafter call the detector a "light detector". The light detector 22 is preferably mounted on the cover member 20 of the light-tight enclosure 4 and connected to the data processing system. It is possible within the scope of the invention to have interchangeable detectors so that light emission from the small animal may be captured in different forms or with different devices during the course of the experiment or plurality of experiments. It is further possible to include interchangeable filters that are positioned between the detector 22 and the small animal to enable capturing of light at selected wavelengths, depending on the experiment being performed and the bioluminescent or fluorescent markers being used therefor. The latter would also allow multiple experiments to be performed on a small animal by intermittently exchanging filters. The filters (not shown) may be positioned adjacent or close to the detector face and held in a rotating or drawer cassette mechanism remotely actuatable for sliding the chosen filter in front of the detector face or retracting it away from the detector face, respectively. The filters may be positioned and actuated in the same manner as the shutter 21 and interchangeable therewith.

The bioluminescence detector system 6 advantageously further comprises a light-funneling device comprising a light-funneling member 24 that extends from the light detector 22 in a tapered diverging manner towards the base member 16 and is configured to minimize internal loss of light and to improve channeling of bioluminescence-emitted light from the small animal to the light-collecting face 40 of the light detector 22. The light-funneling member 24 may advantageously have a substantially conical shape, although slight deviations from a conical shape, such as a slightly curved (concave or convex) generating line of the tapered shape, may also be implemented. Where the light detector is a light intensity measuring device such as a PMT, then the light-funneling member advantageously has a surface 42 that is light-reflecting or light-diffusing or a combination of part reflecting and part diffusing. A reflecting surface may comprise for example a shiny metalized surface, so that bioluminescent light emitted by the small animal that is directed towards the side walls of the light-tight enclosure is reflected to the extent possible towards the light detector 22. Instead of a metalized reflective surface, the light funneling member may also have a light diffusive surface, such as a white colored surface. A diffusive surface has the advantage of redistributing light in a manner that reduces the variation in the light detection measurement dependent on the position of the small animal on the base 16.

The light-funneling device may further comprise a central light-redirecting surface 26 on the center portion 38 extending from the base member 16, for example in the form of a cone, with a surface that is light-reflecting or light-diffusing or a combination of part reflecting and part diffusing that re-directs bioluminescence from the small animal towards the surface 42 of light-funneling member 24. The center portion 38 may have the shape of a cone as illustrated, or of a protrusion of various generally tapered or rounded shapes, for example a bullet head shape that is configured for re-directing as much light emitted from the small animal as possible towards the surface 42 of the external light-funneling member 24. The central light-redirecting surface 26 also helps to redirect some of the light reflected off the light-funneling member 24 upward toward the detector system.

The above-described light-funneling device advantageously allows detection of very low levels of bioluminescence by minimizing loss of light radiated laterally (i.e., not in the direction of the light detector). This provides greater sensitivity in measuring low levels of bioluminescence, or allows for the use of less luciferin or another substrate to be administered to the small animal to produce bioluminescence.

For experiments or parts of experiments that rely on a camera as the light detector, the surfaces of the light-funneling device may comprise a light-absorbing surface, such as a matt black surface, in order to avoid diffusion and reflection, thus improving direct visualization of the small animal by the camera. In this regard, the light-funneling device 24 may advantageously be removably mounted in the light-tight enclosure 4 so as to be interchangeable. Alternatively, a remotely actuatable light-absorbing curtain (not shown) may be mounted inside the cone 24 and configured to be drawn around so as to cover the reflective surface 42 for camera detection and to be opened so as to uncover the reflective surface for photon detection, thus avoiding having to open the light-tight enclosure and interchange the light-funneling device.

Examples of the fields of application of the present invention are:
- measurement of ultradian, circadian and infradian gene expression in internal organs;
- measurement of gene expression of cell cycle in healthy and cancerous tissues;
- measurement of gene expression for genes involved in the control of metabolism (e.g., target genes of PPARα, β, γ, SREBPS, insulin, glucagon, AMPK, LKB, PGC-1) in healthy and sick animals (obese, diabetic, cancerous);
- measurement of gene expression for genes involved in drug metabolism (e.g., coding for regulators and enzymes involved in xenobiotic detoxification, such as constitutive androstane receptor, cytochrome p 450, esterases, HSF1, etc.);
- measurement of gene expression for genes related to physical exercise (e.g., running on a treadmill) in different tissues (muscle, liver, adipose tissue); and
- measurement of fluorescence, for example of fluorescent proteins such as green fluorescent protein (GFP), red fluorescent protein (RFP), and cyan fluorescent protein (CFP).

The invention claimed is:

1. An apparatus for real-time in vivo bioluminescence monitoring in a conscious small animal, comprising a light-tight enclosure comprising a base, side wall and cover configured for housing the conscious small animal such that the conscious small animal may move freely, a bioluminescence detector system comprising a light detector for detecting the light emitted by said conscious small animal connected to a data processing system, and a life-sustaining system configured for maintaining the conscious small animal alive for a prolonged period of time spanning from a few days to a few weeks, wherein the apparatus further comprises a light funneling device comprising a light funneling member that extends from the light detector in a diverging manner towards the base, the light funneling member comprising a surface directed towards the base, wherein the surface is light reflecting or light diffusing or a combination of part reflecting and part diffusing, wherein the light funneling device further comprises a central light-redirecting surface extending from the base comprising a surface that is light reflecting or light diffusing or a combination of part reflecting and part diffusing configured to re-direct light emitted from the conscious small animal towards the surface of the light funneling member.

2. The apparatus according to claim 1, wherein the life-sustaining system comprises a remotely controllable ventilation system connected to the data processing system.

3. The apparatus according to claim 1, wherein the apparatus comprises a temperature sensor configured to measure the environmental temperature in the light-tight enclosure and a heat exchanger connected to the data processing system and configured to control the environmental temperature in the light-tight enclosure.

4. The apparatus according to claim 1, wherein the life-sustaining system comprises a remotely controllable source of light connected to the data processing system.

5. The apparatus according to claim 1, wherein the life-sustaining system comprises a remotely controllable and actionable food delivery device connected to the data processing system.

6. The apparatus according to claim 5, wherein the food delivery device comprises a feeding tube in which may be inserted food, the feeding tube comprising a window at a bottom end of the tube proximate a base of the light-tight enclosure configured for providing access to the food, the food delivery device further comprising a food access closure device remotely actuatable to close access to food through the window.

7. The apparatus according to claim 6, wherein the food access closure device comprises a closure tube coaxially and slidably mounted around the feeding tube and coupled to a remotely controlled actuator configured to lift or to rotate the closure tube to open or close the feeding window.

8. The apparatus according to claim 5, wherein the food is in the form of pellets stacked vertically, the lowest pellet resting on a bottom end of the tube positioned at or above the base.

9. The apparatus according to claim 1, wherein the light funneling member has a substantially conical shape.

10. The apparatus according to claim 1, wherein the central light-redirecting surface comprises the shape of a cone or a generally tapered shape.

11. The apparatus according to claim 1, wherein the light-tight enclosure is generally cylindrical.

12. The apparatus according to claim 1, wherein the light detector comprises a photomultiplier tube (PMT).

13. The apparatus according to claim 1, further comprising an animal activity related system comprising:
   a movement detector; and/or
   an activity station.

14. The apparatus according to claim 1, wherein the delivery of food, liquid, light, and heat in the light-tight enclosure are controlled by the data processing system.

15. The apparatus of claim 1, wherein the surface of the light funneling member is configured to minimize internal loss of light and to channel the light emitted from the conscious small animal to the light detector.

16. A method for non-invasive real-time in vivo bioluminescence monitoring in a conscious small animal comprising:
   placing a conscious small animal expressing a luminescent reporter gene under the control of a gene of interest in an apparatus according to claim 1; and
   monitoring the light emitted by said conscious small animal which is detected by the bioluminescence detector system.

17. The method according to claim 16, wherein the conscious small animal placed into said apparatus is a rodent, an amphibian, a reptile or a bird.

18. The method according to claim 16, wherein said luminescent reporter gene is the gene encoding a luciferase.

19. The method according to claim 16, wherein said conscious small animal is a transgenic animal or an animal in which at least one organ or tissue has been transduced with a vector harboring a luminescent reporter gene under the control of a gene of interest.

20. The method according to claim 16, wherein the conscious small animal has been injected with a substrate of the luminescent reporter gene's product prior to placing said animal in the light-tight enclosure.

* * * * *